United States Patent [19]

LaZonby et al.

[11] Patent Number: 5,198,453

[45] Date of Patent: Mar. 30, 1993

[54] GLUTARALDEHYDE PLUS 2-(THIOCYANOMETHLTHIO)-BENZO-THIAZOLE AS A BIOCIDE FOR INDUSTRIAL WATERS

[75] Inventors: Judy LaZonby, Crystal Lake; Harley R. Melo, Itasca, both of Ill.

[73] Assignee: Nalco Chemical Company, Naperville, Ill.

[21] Appl. No.: 856,798

[22] Filed: Mar. 24, 1992

[51] Int. Cl.$^5$ ............................................. C02F 1/68
[52] U.S. Cl. .................................. 514/367; 514/705; 162/161; 210/764
[58] Field of Search ........................... 210/764; 71/67; 162/161; 514/705, 367

[56] References Cited

U.S. PATENT DOCUMENTS 4,539,071 9/1985 Clifford et al. ..................... 162/161
5,000,618 3/1991 Greenley ............................. 210/501

OTHER PUBLICATIONS

Abstract (Basic) U.S. Pat. No. 4,802,996, Nalco Chemical Company, Feb. 7, 1989 Mouche, R. J./Lin, M. J.—Control of Sulfate Reducing Bacteria in Flue Gas Scrubbing Sludges to Prevent Hydrogen Sulphide Release.
Abstract (Basic): JP 86232864, Sep. 30, 1986, Kurita Water Ind. KK, Industrial Germicide-Contains Glutaraldehyde and Methylene-Bis-Thiocyanate, Giving Synergistic Activity.
Abstract (Basic): EP0261607 Nalco Chemical Company; Mar. 30, 1988, Mouche, R. J.; Lin, M. J. Control of Sulphate-Reducing Bacteria in Industrial Waste Waters by Addn. of Glutaraldehyde.
Abstract (Basic): AU 8774295; Jan. 7, 1988, Nalco Chemical Company, Lamarre, T. M.; Martin C. H. Synergistic Compsn. for Controlling Bacteria and Fungi in Water Contg. Tributyl-Tetradecyl . . . .
U.S. Pat. No. 4,800,235; Nalco Chemical Company; Jan 24, 1989; Lamarre, T. M., Martin, C. H.; Synergistic Compsn. for Controlling Bacteria and Fungi in Water Contg. 1,5-Pentanedial and Mixt. of Alkyl-Methyl-Benzyl-Ammonium Chloride Cpds. (Abstract).
U.S. Pat. No. 4,539,071; Sep. 3, 1985; Clifford/Birchall; Synergistic Biocide for Cooling Water Systems or Water Systems in Paper Manufacture Contg. Glutaraldehyde and an Isothiazolone. (Abstract).
Synergistic Biocidal Compsn. for Treating Industrial Process Waters-Comprises Tributyl Tetradecyl Phosphonium Chloride and 1,5-Pentane-Dial; CA1269300; A; May 22, 1990; 9027 (Abstract).
U.S. Pat. No. 4,920,141 Petrolite Corp. Horstman/-Jones; Apr. 24, 1990, Composition for Inhibiting Growth of Sulphate-Reducing Bacteria-Comprises Mixture of Glutaraldehyde and E.G.Metronidazole (Abstract).
Abstract (Basic): JP01272506; Oct. 31, 1989; Somar Corporation Antimicrobial(s) for Paper Pulp Industry-Contg. e.g. 2-Methyl-3-Isothiazolone and Glutaraldehyde in Complex.

*Primary Examiner*—Stanley S. Silverman
*Assistant Examiner*—Cynthia L. Nessler
*Attorney, Agent, or Firm*—Robert A Miller; John G. Premo

[57] ABSTRACT

A method for controlling microorganisms in industrial process waters which comprises treating these waters with a biocidal amount of a composition comprising glutaraldehyde and 2-(thiocyanomethylthio)benzothiazole.

7 Claims, No Drawings

GLUTARALDEHYDE PLUS 2-(THIOCYANOMETHLTHIO)-BENZOTHIAZOLE AS A BIOCIDE FOR INDUSTRIAL WATERS

GENERAL STATEMENT OF THE INVENTION

Glutaraldehyde in combination with TCMTB, 2-(thiocyanomethylthio)benzothiazole, provides superior microorganism control in industrial process water systems. This biocide is particularly effective in controlling the growth and reproduction of microorganisms in paper mill systems.

INTRODUCTION

The formation of slime by microorganisms is a problem which is present in many industrial process water systems. For example, lagoons, lakes, pools, and such systems as cooling water systems and pulp and paper mill systems are environments which favor the growth and reproduction of slime forming microorganisms. In both once-through and recirculating cooling systems which employ large quantities of water as a cooling medium, the formation of slime by microorganisms is an extensive and constant problem.

Airborne organisms are readily entrained in the water from cooling towers and find this warm medium an ideal environment for growth and multiplication. Aerobic and heliotropic organisms flourish on the tower proper while other organisms colonize and grow in such areas as the tower sump and the piping and passages of the cooling system. Such slime serves to deteriorate the tower structure in the case of wooden towers. In addition, the deposition of slime on metal surfaces promotes corrosion. Slime carried through the cooling system plugs and fouls lines, valves, strainers, etc. and deposits on heat exchange surfaces, causing the impedance of heat transfer. In most industrial process waters, especially pulp and paper mill systems, spore forming bacteria and Pseudomonas aeruginosa contribute to slime formation. The latter is most prevalent in paper mill slimes. Fungi is also a contributor towards slime formation. The slime becomes entrained in the paper produced causing breakouts on the paper machines with consequent work stoppages and the loss of production time. Slimes can cause unsightly blemishes in the final product which results in rejects and wasted output. These problems have resulted in the extensive utilization of biocides in pulp and paper mill systems. Materials which have enjoyed widespread use in such applications include chlorine, organo-mercurials, chlorinated phenols, organobromines, and various organo sulfur compounds. All of these compounds are generally useful for this purpose but each has a variety of impediments. For example, chlorination is limited both by its specific toxicity for slime-forming organisms at economic levels and by the ability of chlorine to react which results in the loss of the chlorine before its full biocidal function may be achieved. Other biocides are attended by odor problems and hazards in respect to storage, use or handling which limit their utility. To date, no one compound or type of compound has achieved a clearly established predominance in treating paper mill systems.

Economy is a major consideration in respect to all of these biocides. Such economic considerations attach to both the cost of the biocide and the expense of its application. The cost performance index of any biocide is derived from the basic cost of the material, its effectiveness per unit of weight, the duration of its biocidal or biostatic effect in the system treated, and the ease and frequency of its addition to the system treated. To date, none of the commercially available biocides have exhibited a prolonged biocidal effect. Their effectiveness is rapidly reduced as the result of exposure to physical conditions such as temperature or association with ingredients contained by the system toward which they exhibit an affinity. This results in a restriction or elimination of their biocidal effectiveness.

The use of such biocides involves their continuous or frequent additions to paper mill systems and their additions to a plurality of points or zones in the system. The cost of the biocide and the labor cost are considerable.

In a system experiencing relatively slow flow, such as paper mill, if a biocide is added at the beginning of the system, its biocidal effect may be completely dissipated before it has reached all of the points at which its effect is needed. As a consequence, the biocide must be added at a plurality of points, and even then a gradual loss in effectiveness will be experienced between the point of addition to the system and the next point downstream.

If it were possible to provide a biocide for paper mill systems which was effective in low dosages, was long lasting and did not require feeding at multiple points in the paper making system a valuable contribution to the paper making art would be afforded.

Also of benefit to the art would be the furnishing of a biocide that was effective in controlling microorganisms, particularly, Pseudomonas species which are present in a variety of industrial process waters.

THE INVENTION

The invention resides in a method for controlling microorganisms in industrial process waters which comprises treating such waters with a biocidal amount of a composition comprising of glutaraldehyde and TCMTB combined in a weight ratio of from about 9:1 to 1:19. This composition is particularly effective in controlling *Pseudomonas aeruginiosa* and spore forming bacteria such as *Bacillus subtilis*

DOSAGE AND RATIO OF GLUTARALDEHYDE TO TCMTB

Depending on the particular industrial process water or paper mill system the dosage will vary. It may be as little as 1 part per million by weight to as much as 100 parts per million (ppm). Typical dosages are between 5–50 ppm.

The weight ratio of Glutaraldehyde to TCMTB, as indicated is between about 9:1 to about 1:19. A preferred range is between about 9:1 to 1:1 when the compositions are used to treat paper mill systems.

EVALUATION OF THE INVENTION a) Definition of Synergism

Synergy is mathematically demonstrated by the industry accepted method described by S. C. Kull et al. in *Applied Microbiology*, vol. 9, pages 538–541 (1961). As applied to this invention, it is as follows:

$Q_A$ = the ppm of active of Glutaraldehyde alone which produces an endpoint.

$Q_B$ = the ppm of active TCMTB alone which produces an endpoint.

$Q_a$ = the ppm of active of Glutaraldehyde, in combination, which produces an endpoint.

$Q_b$ = the ppm of active of TCMTB, in combination, which produces an endpoint.

$$\text{if } \frac{Q_a}{Q_A} + \frac{Q_b}{Q_B} = \text{Synergy Index}$$

if Synergy Index (SI) is:
- < 1, it indicates synergy
- = 1, it indicates additivity
- > 1, it indicates antagonism b) Test Procedures Ratio Determination Glutaraldehyde and TCMTB mixtures with ratios ranging from 19:1 to 1:19 were prepared at concentrations of 200 ppm a.i. and used as stock solutions to prepare lower dilutions ranging from 180 ppm to 20 ppm. These dilutions were dispensed into microtiter wells and mixed with equal volumes of paper mill furnish contaminated with naturally occurring environmental organisms. After 4 hours and 24 hours of contact, an aliquot from each well was seeded into a second microtiter plate containing Tryptic Soy Broth and incubated overnight. Minimum inhibitory concentrations (MIC) of biocides were determined from the aliquots with the lowest concentration of biocides which failed to produce growth in the second microliter plate.

Shake Flask

A 1% synthetic furnish prepared from 50% Hardwood/50% Softwood dry lap, clay titanium oxide, alum, rosin, starch and sodium phosphates, mono and dibasic, was seeded with equal amounts of *Pseudomonas aeruginiosa* ATCC#15442 and *Bacillus subtilis* W23 to a concentration of about $1 \times 10^6$ CFU/ml and enriched with 10% Glycerol-Yeast Extract Broth. To this furnish individual biocides and biocide mixtures were added in decreasing concentrations and incubated in flasks at 37° C. in an orbital shaker. At 0, 4, and 24 hours of contact, aliquots from each flask were diluted and plated on Tryptone Glucose Extract (TGE) agar to determine the total number of viable organisms remaining. An endpoint of a 2, 3, 4, or 5 $\log_{10}$ reduction in viable organisms was then selected for calculating synergy.

MiniTox ™

A redox dye, resazurin, was added to the above described synthetic paper furnish and dispensed into a 96 well microliter plate in 0.1 ml aliquots. An equal volume of biocide diluted to 500 ppm was added to the first well in the first row and mixed thoroughly. A 0.1 ml portion of the mixed well was then transferred to the second well in the same row and thoroughly mixed. This process was repeated to the end row resulting in a serial dilution of the biocide down to a 0.125 ppm concentration. A second biocide and subsequent biocide mixtures in various ratios were similarly diluted in the remaining rows. Biologically active organisms cause the resazurin to change from purple to pink, indicating the lowest concentration of biocide that will inhibit biological function. Synergy of the mixtures was calculated as previously described.

EXAMPLE 1

When the two biocides are applied together in a combination product, synergy is being seen with the 4:1 and 1:1, TCMTB:Glut ratios after 24 hours in Neutral Buffered Synthetic Furnish (NBSF).

Results:

| | Biocide (ppm a.i.) TCMTB:Glut | 0 HOUR | 5 HOURS | 24 HOURS |
|---|---|---|---|---|
| 1. | 9:1 - 100(90/10) | $3.8 \times 10^6$ | $<10^1$ | $<10^1$ |
| 2. | 9:1 - 50(45/5) | $5.0 \times 10^6$ | $1.8 \times 10^4$ | $4.2 \times 10^2$ |
| 3. | 9:1 - 25(22/3) | $5.2 \times 10^6$ | $2.2 \times 10^5$ | $2.7 \times 10^5$ |
| 4. | 9:1 - 12.5(11/1.5) | $4.3 \times 10^6$ | $4.4 \times 10^5$ | $5.2 \times 10^6$ |
| 5. | 4:1 - 100(80/20) | $4.4 \times 10^6$ | $<10^1$ | $<10^1$ |
| 6. | 4:1 - 50(40/10) | $5.0 \times 10^6$ | $<10^1$ | $<10^1$ |
| 7. | 4:1 - 25(20/5) | $4.5 \times 10^6$ | $6.2 \times 10^4$ | $1.2 \times 10^5$ |
| 8. | 4:1 - 12.5(10/2.5) | $4.7 \times 10^6$ | $3.5 \times 10^5$ | $7.7 \times 10^6$ |
| 9. | 1:1 - 100(50/50) | $3.9 \times 10^6$ | $<10^1$ | $<10^1$ |
| 10. | 1:1 - 50(25/25) | $5.8 \times 10^6$ | $<10^1$ | $<10^1$ |
| 11. | 1:1 - 25(12.5/12.5) | $5.2 \times 10^6$ | $5.0 \times 10^2$ | $1.4 \times 10^3$ |
| 12. | 1:1 - 12.5(6.25/6.25) | $4.1 \times 10^6$ | $1.8 \times 10^3$ | $2.9 \times 10^6$ |
| 13. | Glut - 100 | $4.5 \times 10^6$ | $<10^1$ | $5.7 \times 10^2$ |
| 14. | Glut - 50 | $4.4 \times 10^6$ | $6 \times 10^1$ | $1.2 \times 10^2$ |
| 15. | Glut - 25 | $6.8 \times 10^6$ | $7 \times 10^1$ | $2.3 \times 10^4$ |
| 16. | Glut - 12.5 | $5.1 \times 10^6$ | $4.9 \times 10^2$ | $2.8 \times 10^5$ |
| 17. | TCMTB - 100 | $5.2 \times 10^6$ | $3.7 \times 10^5$ | $<10^1$ |
| 18. | TCMTB - 50 | $4.4 \times 10^6$ | $3.6 \times 10^5$ | $2.6 \times 10^3$ |
| 19. | TCMTB - 25 | $6.3 \times 10^6$ | $4.7 \times 10^5$ | $3.2 \times 10^4$ |
| 20. | TCMTB - 12.5 | $5.9 \times 10^6$ | $5.2 \times 10^5$ | $1.1 \times 10^6$ |
| 21. | Control - 0 | $7.7 \times 10^6$ | $1.3 \times 10^7$ | $6.0 \times 10^7$ |
| 22. | Control - 0 | $5.2 \times 10^6$ | $1.4 \times 10^7$ | $6.6 \times 10^7$ |

| NBSF-5 hour 4 LOG | SI | NBSF-24 hour | SI |
|---|---|---|---|
| G = 12.5 | | G = >100 (200) | |
| TCMTB = >100 (200) | | TCMTB = 100 | |
| 9:1 = 100 (90/10) | 1.7 | 9:1 = 100 (90/10) | .95 |
| 4:1 = 50 (40/10) | 1.0 | 4:1 = 50 (40/10) | .5 |
| 1:1 = 12.5 (6.5/6.5) | .55 | 1:1 = 50 (25/25) | .5 |

EXAMPLE 2

These ratios were also tested in a pH 7.1 mill furnish from a midwest paper mill. Results indicate that after 4 hours of contact, synergy is seen with the 4:1 and 9:1 ratios. After 24 hours of contact, synergy is seen at all 3 ratios.

| Biocide (ppm a.i.) TCMTB:Glut | 0 Hours | 4 Hours | 24 Hours |
|---|---|---|---|
| 1. 9:1 - 100 (90/10) | $1.5 \times 10^6$ | $2.4 \times 10^2$ | $6.0 \times 10^1$ |
| 2. 9:1 - 50 (45/5) | $2.4 \times 10^6$ | $1.6 \times 10^2$ | $5.8 \times 10^2$ |
| 3. 9:1 - 25 (22.5/2.5) | $2.5 \times 10^6$ | $1.8 \times 10^3$ | $2.5 \times 10^6$ |
| 4. 9:1 - 12.5(11.25/1.25) | $4.2 \times 10^6$ | $1.1 \times 10^5$ | $7.0 \times 10^7$ |
| 5. 4:1 - 100 (80/20) | $3.5 \times 10^6$ | $1.8 \times 10^2$ | $4.0 \times 10^1$ |
| 6. 4:1 - 50 (40/10) | $3.6 \times 10^6$ | $1.8 \times 10^2$ | $4.2 \times 10^2$ |
| 7. 4:1 - 25 (20/5) | $2.9 \times 10^6$ | $4.7 \times 10^2$ | $2.9 \times 10^7$ |
| 8. 4:1 - 12.5(10/2.5) | $3.2 \times 10^6$ | $2.3 \times 10^5$ | $9.1 \times 10^7$ |
| 9. 1:1 - 100 (50/50) | $3.9 \times 10^6$ | $2.4 \times 10^2$ | $1 \times 10^1$ |
| 10. 1:1 - 50 (25/25) | $3.1 \times 10^6$ | $2.1 \times 10^2$ | $8 \times 10^1$ |
| 11. 1:1 - 25 (12.5/12.5) | $2.9 \times 10^6$ | $2.3 \times 10^2$ | $2.9 \times 10^5$ |
| 12. 1:1 - 12.5(6.25/6.25) | $4.8 \times 10^6$ | $9.0 \times 10^3$ | $7.6 \times 10^7$ |
| 13. Glut - 100 | $2.3 \times 10^6$ | $1.6 \times 10^2$ | $<10^1$ |
| 14. Glut - 50 | $2.6 \times 10^6$ | $1.3 \times 10^2$ | $<10^1$ |
| 15. Glut - 25 | $3.5 \times 10^6$ | $1.7 \times 10^2$ | $2.3 \times 10^5$ |
| 16. Glut - 12.5 | $4.2 \times 10^6$ | $4.3 \times 10^2$ | $2.9 \times 10^7$ |
| 17. TCMTB - 100 | $3.5 \times 10^6$ | $3.8 \times 10^2$ | $1.8 \times 10^7$ |
| 18. TCMTB - 50 | $3.1 \times 10^6$ | $1.4 \times 10^3$ | $2.8 \times 10^7$ |
| 19. TCMTB - 25 | $3.5 \times 10^6$ | $4.8 \times 10^4$ | $3.2 \times 10^7$ |
| 20. TCMTB - 12.5 | $3.5 \times 10^6$ | $2.7 \times 10^6$ | $8.2 \times 10^7$ |
| 21. Control 0 | $5.4 \times 10^6$ | $8.8 \times 10^7$ | $5.5 \times 10^7$ |
| 22. Control 0 | $4.3 \times 10^6$ | $9.5 \times 10^7$ | $6.6 \times 10^7$ |

| AT 24 hours - 5 Log Drop | SI | AT 4 hours - 5 Log Drop | SI |
|---|---|---|---|
| Glut = 50 | | Glut = 12.5 | |
| TCMTB = >100-200 | | TCMTB = 100 | |
| 9:1 = 50 (45/5) | .55 | 9:1 = 50 (45/5) | .85 |
| 4:1 = 50 (40/10) | .6 | 4:1 = 25 (20/5) | .6 |

-continued

| | | | |
|---|---|---|---|
| 1:1 = 50 (25/25) | .75 | 1:1 = 25 (12.5/12.5) | >1 |

EXAMPLE 3

Using a second midwestern mill furnish at pH 7.0, excellent synergy was seen with the 3 ratios tested. At 1:1, 1:4, and 1:9, TCMTB:Glutaraldehyde, better bacterial control was seen with 50 ppm a.i. of either blend than with 100 ppm a.i. of pure Glutaraldehyde.

| Biocide (ppm a.i.) | 0 Hour | 5 Hour | 24 Hour |
|---|---|---|---|
| Glut - 100 | $3.2 \times 10^8$ | $8.5 \times 10^3$ | $1.5 \times 10^3$ |
| 50 | $3.0 \times 10^8$ | $1.8 \times 10^5$ | $3.4 \times 10^8$ |
| 25 | $2.8 \times 10^8$ | $1.4 \times 10^8$ | $2.6 \times 10^8$ |
| 12.5 | $3.4 \times 10^8$ | $1.0 \times 10^8$ | $3.1 \times 10^8$ |
| TCMTB - 100 | $2.7 \times 10^8$ | $4.4 \times 10^8$ | $2.8 \times 10^7$ |
| 50 | $3.5 \times 10^8$ | $1.0 \times 10^8$ | $3.8 \times 10^7$ |
| 25 | $3.0 \times 10^8$ | $1.2 \times 10^8$ | $6.4 \times 10^7$ |
| 12.5 | $3.6 \times 10^8$ | $1.9 \times 10^8$ | $1.1 \times 10^8$ |
| TCMTB:Glut | | | |
| 1:1 - 100 (50/50) | $3.0 \times 10^8$ | $1.6 \times 10^3$ | $1.0 \times 10^3$ |
| 50 (25/25) | $3.1 \times 10^8$ | $2.1 \times 10^3$ | $1.4 \times 10^3$ |
| 25 (12.5/12.5) | $3.0 \times 10^8$ | $1.3 \times 10^7$ | $1.2 \times 10^7$ |
| 12.5 (6.25/6.25) | $2.8 \times 10^8$ | $2.8 \times 10^8$ | $8.3 \times 10^7$ |
| 1:4 - 100 (20/80) | $3.0 \times 10^8$ | $1.3 \times 10^3$ | $7.8 \times 10^2$ |
| 50 (10/40) | $2.8 \times 10^8$ | $1.7 \times 10^3$ | $9.4 \times 10^2$ |
| 25 (5/20) | $3.0 \times 10^8$ | $4.2 \times 10^7$ | $2.0 \times 10^8$ |
| 1:4 12.5(2.5/10) | $3.0 \times 10^8$ | $2.1 \times 10^8$ | $2.6 \times 10^8$ |
| 1:9 - 100 (10/90) | $2.6 \times 10^8$ | $1.1 \times 10^3$ | $8.4 \times 10^2$ |
| 50 (5/45) | $2.3 \times 10^8$ | $3.2 \times 10^3$ | $2.4 \times 10^3$ |
| 25(2.5/22.5) | $2.8 \times 10^8$ | $6.2 \times 10^7$ | $2.0 \times 10^8$ |
| 12.5(1.25/11.25) | $2.6 \times 10^8$ | $4.4 \times 10^8$ | $2.6 \times 10^8$ |

Synergy Calculation

After 24 hours of contact, a 5 log or greater reduction

| Biocide | SI |
|---|---|
| Glut = 100 | |
| TCMTB = >100 (200) | |
| 1:1 = 50 (25/25) | .375 |
| 1:4 = 50 (10/40) | .45 |
| 1:9 = 50 (45/5) | .475 |

EXAMPLE 4

The MIC for the optimum antibacterial synergistic ratios was performed and indicated that maximum synergy occurs after 24 hours of contact.

| Biocide | MIC in ppm a.i. | SI |
|---|---|---|
| 4 Hour Contact | | |
| TCMTB | 80 | |
| Glut | 20 | |
| TCMTB:Glut | | |
| 19:1 | 90 | 1.2 |
| 9:1 | 80 | 1.3 |
| 4:1 | 50 | 1.0 |
| 1:1 | 20 | .63 |
| 1:4 | 20 | .85 |
| 1:9 | 10 | .46 |
| 24 Hour Contact | | |
| TCMTB | 70 | |
| Glut | 20 | |
| TCMTB:Glut | | |
| 19:1 | 40 | .64 |
| 9:1 | 40 | .71 |
| 4:1 | 40 | .85 |
| 1:1 | 20 | .64 |
| 1:4 | 20 | .85 |
| 1:9 | 20 | .92 |

EXAMPLE 5

Synergistic activity against fungi was also demonstrated in this furnish from a Maine papermill after 24 hours of contact.

| Biocide (ppm a.i.) | 1 Hour | 5 Hour | 24 Hour |
|---|---|---|---|
| Glut - 100 | $2.0 \times 10^2$ | $2.0 \times 10^2$ | $1.8 \times 10^1$ |
| 50 | $1.4 \times 10^3$ | $1.0 \times 10^2$ | $6.3 \times 10^1$ |
| 25 | $1.8 \times 10^3$ | $2.0 \times 10^2$ | $5.9 \times 10^3$ |
| 12.5 | $1.8 \times 10^3$ | $1.2 \times 10^3$ | $2.5 \times 10^4$ |
| TCMTB - 100 | $6.0 \times 10^2$ | $<10^0$ | $<10^0$ |
| 25 | $1.4 \times 10^3$ | $1 \times 10^0$ | $<10^0$ |
| 12.5 | $2.0 \times 10^3$ | $3 \times 10^2$ | $4 \times 10^0$ |
| 6.25 | $1.7 \times 10^3$ | $7.0 \times 10^2$ | $8 \times 10^0$ |
| TCMTB:Glut | | | |
| 4:1 - 100 | $2.0 \times 10^2$ | $<10^0$ | $<10^0$ |
| 50 | $1.4 \times 10^3$ | $<10^0$ | $<10^0$ |
| 25 | $1.4 \times 10^3$ | $2 \times 10^0$ | $<10^0$ |
| 12.5 | $1.9 \times 10^3$ | $2 \times 10^0$ | $5 \times 10^0$ |
| 1:1 - 100 | $5 \times 10^2$ | $<10^0$ | $<10^0$ |
| 50 | $6 \times 10^2$ | $3 \times 10^1$ | $<10^0$ |
| 25 | $1.3 \times 10^3$ | $1.0 \times 10^2$ | $<10^0$ |
| 12.5 | $1.9 \times 10^3$ | $4.0 \times 10^2$ | $3.1 \times 10^1$ |
| 1:4 - 100 | $9 \times 10^2$ | $8 \times 10^0$ | $<10^0$ |
| 50 | $6.0 \times 10^2$ | $<10^0$ | $<10^0$ |
| 25 | $2.4 \times 10^3$ | $2.7 \times 10^1$ | $1.2 \times 10^3$ |
| 12.5 | $2.2 \times 10^3$ | $1.2 \times 10^3$ | $1.2 \times 10^3$ |
| Control - 0 | $2.2 \times 10^3$ | $1.6 \times 10^3$ | $2.2 \times 10^3$ |
| 0 | $2.3 \times 10^3$ | $2.6 \times 10^3$ | $2.6 \times 10^3$ |

| Synergy Calculations (for 24 hour data): | |
|---|---|
| Biocide | SI |
| Glut = >100 (200) | |
| TCMTB = 25 | |
| 4:1 = 25 (20/5) | .85 |
| 1:1 = 25 (12.5/12.5) | .63 |
| 1:4 = 50 (10/40) | .60 |

We claim:

1. A method of controlling the growth of microorganisms in industrial process waters which comprises treating such waters with a synergistic biocidal amount of a biocidally active composition comprising glutaraldehyde and 2-(thiocyanomethylthio)benzothiazole combined in a weight ratio of from 9:1 to 1:19.

2. The method of claim 1 where the industrial process water is the water of a paper mill system.

3. The method of claim 1 where the microorganisms contain *Pseudomonas aeruginosa*.

4. The method of claim 1 where the weight ratio of glutaraldehyde to 2-(thiocyanomethylthio)benzothiazole is 9:1 to 1:1.

5. The method of claim 2 where the microorganisms are spore forming bacteria.

6. The method of claim 2 where the ratio of glutaraldehyde to 2-(thiocyanomethylthio)benzothiazole is 9:1 to 1:1.

7. The method of claim 1 where the microorganisms contain fungi.

* * * * *